(12) United States Patent
Jahnke et al.

(10) Patent No.: US 9,310,312 B2
(45) Date of Patent: Apr. 12, 2016

(54) APPARATUS AND METHOD FOR AUTOMATIC INSPECTION OF THROUGH-HOLES OF A COMPONENT

(75) Inventors: Ronny Jahnke, Falkensee (DE); Tristan Sczepurek, Berlin (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 128 days.

(21) Appl. No.: 13/818,105

(22) PCT Filed: Sep. 14, 2011

(86) PCT No.: PCT/EP2011/065906
§ 371 (c)(1),
(2), (4) Date: Feb. 21, 2013

(87) PCT Pub. No.: WO2012/035045
PCT Pub. Date: Mar. 22, 2012

(65) Prior Publication Data
US 2013/0163849 A1    Jun. 27, 2013

(30) Foreign Application Priority Data
Sep. 14, 2010   (EP) ..................................... 10176521

(51) Int. Cl.
*G06K 9/00* (2006.01)
*G01N 21/88* (2006.01)
*G01N 25/72* (2006.01)
*G06T 7/00* (2006.01)

(52) U.S. Cl.
CPC ............ *G01N 21/8851* (2013.01); *G01N 25/72* (2013.01); *G06T 7/0004* (2013.01); *G06T 7/0081* (2013.01); *G06T 7/0097* (2013.01); *G06T 2207/10048* (2013.01); *G06T 2207/30164* (2013.01)

(58) Field of Classification Search
None
See application file for complete search history.

(56) References Cited

U.S. PATENT DOCUMENTS

| 5,111,046 | A |   | 5/1992 | Bantel |
| 5,604,819 | A | * | 2/1997 | Barnard ........................ 382/151 |
| 5,982,927 | A | * | 11/1999 | Koljonen ....................... 382/168 |
| 6,167,167 | A | * | 12/2000 | Matsugu et al. ............... 382/283 |

(Continued)

FOREIGN PATENT DOCUMENTS

| CN | 1602236 A | 3/2005 |
| CN | 1924534 A | 3/2007 |
| EP | 1431754 A2 | 6/2004 |

*Primary Examiner* — Stephen R Koziol
*Assistant Examiner* — Sean Conner (57) ABSTRACT

An apparatus and a method for automatic inspection of through-holes of a component is provided. The proposed apparatus includes an imaging module, an image processing module and an analysis module. The imaging module generates a thermographic image of the component by passing a medium through the through-holes and capturing infra-red radiation emitted from the component while the medium is flowing through the through-holes. The image processing module fits the thermographic image on a digital image obtained from geometrical data of the component. The image processing module is further masks the fitted thermographic image using a digital image mask to extract regions corresponding to through-holes in the thermographic image. The digital image mask is computed based on a determination of positions of through-holes on the digital image. The analysis module evaluates the masked thermographic image to determine an irregularity or blockage in one or more of the through-holes.

15 Claims, 7 Drawing Sheets

(56) References Cited

U.S. PATENT DOCUMENTS

| | | | | |
|---|---|---|---|---|
| 6,317,513 | B2* | 11/2001 | Michael et al. | 382/145 |
| 6,751,343 | B1* | 6/2004 | Ferrell et al. | 382/145 |
| 6,970,578 | B1* | 11/2005 | Strand | 382/103 |
| 7,991,216 | B2* | 8/2011 | Lin et al. | 382/141 |
| 8,483,488 | B2* | 7/2013 | Richter et al. | 382/216 |
| 2002/0076097 | A1* | 6/2002 | Vaidyanathan | 382/154 |
| 2002/0168116 | A1* | 11/2002 | Takayama et al. | 382/275 |
| 2004/0120383 | A1* | 6/2004 | Kennedy et al. | 374/57 |
| 2005/0008215 | A1* | 1/2005 | Shepard | 382/141 |
| 2005/0044519 | A1* | 2/2005 | Sengupta et al. | 716/11 |
| 2005/0190959 | A1* | 9/2005 | Kohler | G01R 31/2813 382/147 |
| 2006/0191622 | A1* | 8/2006 | Ritter et al. | 156/64 |
| 2007/0098248 | A1* | 5/2007 | Toyoda | G06T 7/001 382/145 |
| 2007/0290134 | A1* | 12/2007 | Key et al. | 250/340 |
| 2009/0219379 | A1* | 9/2009 | Rossato et al. | 348/14.01 |
| 2010/0117672 | A1* | 5/2010 | Portune | 324/758 |
| 2010/0118137 | A1* | 5/2010 | Avila et al. | 348/125 |
| 2010/0124369 | A1* | 5/2010 | Wu et al. | 382/141 |
| 2011/0125423 | A1* | 5/2011 | Allen et al. | 702/47 |
| 2011/0235672 | A1* | 9/2011 | Shepard et al. | 374/45 |

* cited by examiner

APPARATUS AND METHOD FOR AUTOMATIC INSPECTION OF THROUGH-HOLES OF A COMPONENT

CROSS REFERENCE TO RELATED APPLICATIONS

This application is the US National Stage of International Application No. PCT/EP2011/065906, filed Sep. 14, 2011 and claims the benefit thereof. The International Application claims the benefits of European Patent Office application No. 10176521.2 EP filed Sep. 14, 2010. All of the applications are incorporated by reference herein in their entirety.

FIELD OF INVENTION

The present invention relates to inspection of through-holes of a component, and in particular, to a method and apparatus for automatic inspection of through-holes of a component using thermography.

BACKGROUND OF INVENTION

In several industrial applications, components having through-holes need to be inspected for proper functioning of the component. One such example is a turbomachine blade or vane. Turbomachines, particularly gas turbines, have vanes and blades that contain channels or through-holes which lead from an exterior surface of the blade or vane to a hollow interior (plenum). In use, pressurized air is applied to the plenum causing cooling airstreams to flow through the through-holes, thereby absorbing heat from the walls of the through-holes, as well as from the surface of the blade or vane, thereby cooling the blade or vane.

In order to function properly, these through-holes, called cooling holes, must be made to a known configuration because the distribution of airflow must be controlled in order to achieve proper cooling. Accordingly, the cooling holes must not be blocked, not even partially. This requires a reliable technique for inspection of the cooling holes to detect blockages from the external surface. If a cooling hole is detected to be blocked, even partially, it may require the component (i.e., the blade or vane) to be discarded and replaced.

Currently checking and inspection of cooling holes of blades or vanes of a gas turbine is done by using infrared thermography. Herein, a medium, generally a hot gas, is forced through the cooling holes and an infra-red camera is used to capture infra-red radiation emitted by the component while the medium is flowing through the cooling holes, to form a thermographic image. Blocked cooling holes obstruct the flow of heat, which is visible in the thermographic image.

Thus, to decide whether or not the component can continue to be used, an evaluation of the thermographic image is required. Currently, the evaluation of thermographic images to detect blocked cooling holes is done manually by trained personnel. This requires individual contrast adjustments for the individual thermographic images, recognition of irregularities in pattern of the cooling holes in the component, counting the rows of hot spots (which correspond to cooling holes) in the thermographic image, and a comparison with the cooling hole pattern in the actual component. Often, it is also necessary to insert a diameter measurement gage or a pin into a cooling hole to inspect irregularities.

Further, evaluation of the thermographic images with standard image processing procedures is not possible because of high noise components in these images and also due to inhomogeneous illumination in the thermographic images due to curvatures in the component.

SUMMARY OF INVENTION

The object of the present invention is to provide a method and an apparatus for automatic inspection of through-holes of a component based on an evaluation of thermographic images which obviates the need for a subjective evaluation as done in the state of the art.

The above object is achieved by the method according to the claims and the apparatus according to the claims.

The underlying idea of the present invention is to provide an automatic evaluation of a thermographic image by correlating the thermographic to a digital image obtained from geometrical data of the component. Using the digital image of the component, a digital image mask is computed based on a determination of the positions of through-holes in the digital image. The thermographic image is fitted on to the digital image and the regions corresponding to through-holes in the thermographic image are extracted using the computed digital image mask. A blockage or irregularity in the through-hole is determined by evaluating this masked thermographic image. One of problems with the existing state of the art is that thermographic images have high noise component and hence it is difficult to identify and analyze through-holes using standard image processing techniques. This problem is solved herein by the use of the above-mentioned digital image mask, to extract the through-holes in the thermographic image. The above method is completely automatic and is considered to be advantageous over the subjective evaluation of thermographic images in the mentioned state of the art.

In one embodiment, said digital image is obtained from a CAD model of the component. In this embodiment, the expected positions of the through-holes can be directly obtained from position data in the CAD model.

In an alternate embodiment, said digital image is obtained from a three-dimensional geometrical measurement of the component. This obviates the need for three-dimensional CAD models and is further not sensitive to deviations in the geometry. The above embodiment thus provides a universal test procedure with very little effort for setting up.

In a further advantageous embodiment, the three-dimensional geometrical measurement of the component is made in-situ with the capturing of the thermographic image and at a viewing position that corresponds to a viewing position of the thermographic image.

In one embodiment, the step of fitting comprises fitting the thermographic image directly on a three-dimensional digital image of the component. This eliminates the additional step of creating a two-dimensional image for fit with the thermographic image. This embodiment is particularly advantageous if the clamping or positioning of the component is reproducible, which allows the test set up to be calibrated or measured just once.

In an alternate embodiment, the step of fitting comprises fitting the thermographic image on a two-dimensional digital image of the component corresponding to an viewing position of the thermographic image view. This embodiment is used when a fixed calibration of the test set-up is not possible.

In a further embodiment, a blockage or irregularity in a particular through-hole is determined by comparing a temperature of that through-hole as indicated in the masked thermographic image to a reference temperature value. In principle, during thermographic imaging when a heated medium is forced into the through-holes, the through-holes act as black-body cavity radiators and as such, they approach behaving as idealized sources of radiation. A blockage in the through hole thus reduces the temperature of the through-hole, which is visible in the thermographic image.

In a further embodiment, for increased contrast, the thermographic image is generated based on a combination of multiple thermographic images including at least a first and a second thermographic image, wherein:

the first thermographic image is generated by passing a heated medium through the through-holes during a heat-up cycle and capturing infra-red radiation emitted from the component during said heat-up cycle, and the second thermographic image is generated by passing a cooled medium through the through-holes during a cool-down cycle and capturing infra-red radiation emitted from the component during said cool-down cycle.

When both a heat-up cycle and a cool-down cycle are analyzed in tandem, is possible to obtain increased contrast or sensitivity in the thermographic image, which can be used to detect partial blockages or other minor irregularities in the through-holes.

In an exemplary embodiment, said component is a turbomachine blade or vane, and wherein said through-holes are cooling holes. Cooling holes in turbine blades or vanes have extremely small dimensions, which makes a manual evaluation of thermographic images rather time consuming and labor intensive. The use of the present invention herein reduces the testing time and eliminates the need of trained personnel for this purpose.

The present invention may also be embodied as a program product comprising computer readable media having computer readable program code stored therein, which, when executed on one or more processors, carries out the method according to any of the above-mentioned embodiments.

BRIEF DESCRIPTION OF THE DRAWINGS

The present invention is further described hereinafter with reference to illustrated embodiments shown in the accompanying drawings, in which.

DETAILED DESCRIPTION OF INVENTION

The embodiments described below illustrate the use of the present invention for automatic inspection of cooling holes of a turbomachine blade or vane of the type mentioned above. However, the present invention may be used for several other industrial applications that involve automatic inspection of through-holes of a component.

Figure 1:
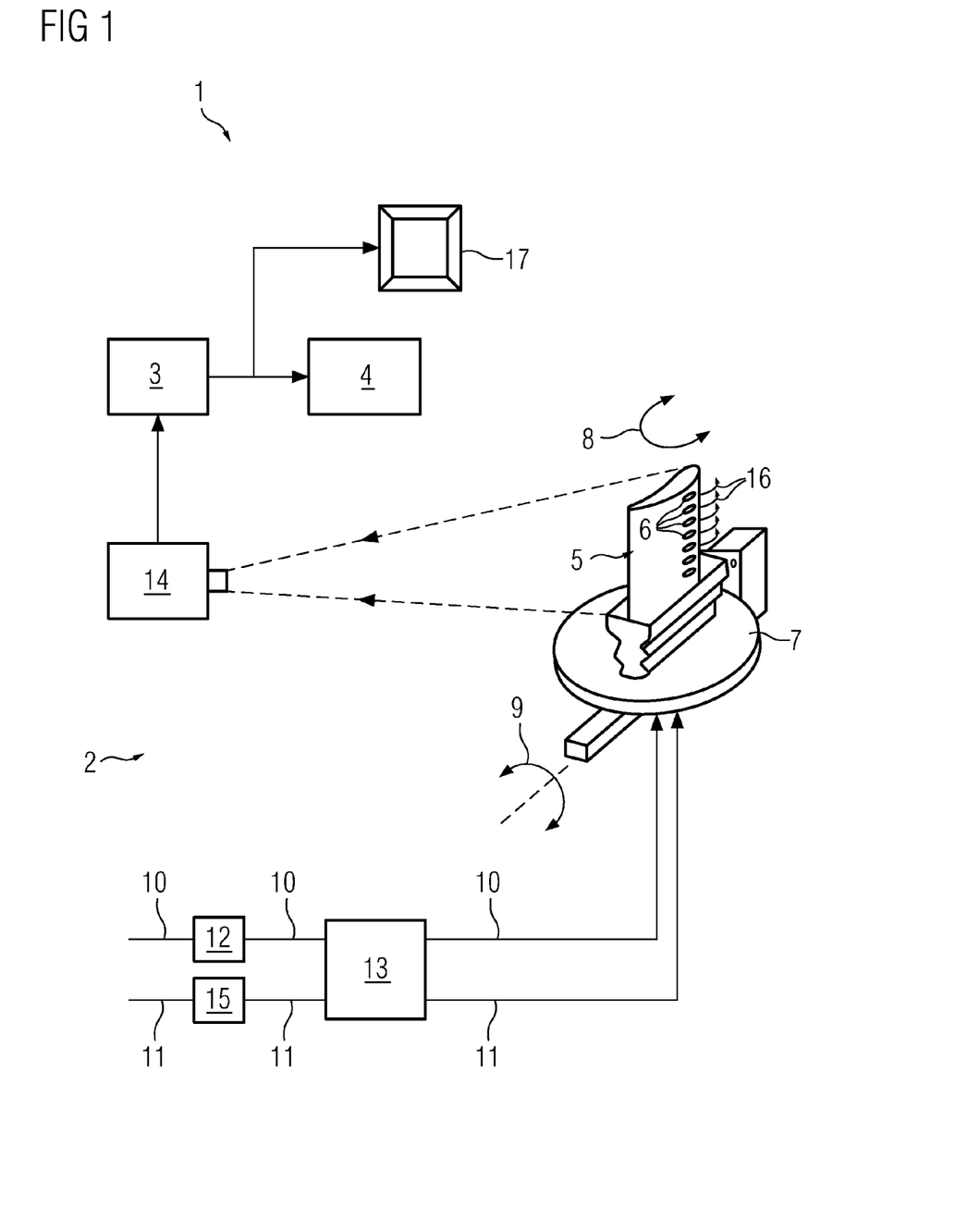
FIG. 1 is a schematic diagram of an apparatus for inspection of through-holes of a component in accordance with one embodiment of the present invention.

Referring to FIG. 1 is illustrated an apparatus 1 for inspecting through-holes 6 formed in a component 5. In this example, the component 5 is a turbine blade or vane, and the through-holes 6 include cooling holes. The apparatus 1 broadly includes an imaging module 2 for generating a thermographic image of the blade or vane 5, an image processing module 3 for extracting regions corresponding to cooling holes from the thermographic image, and an analysis module 4 for evaluating this extracted portion of the thermographic image to determine the presence of a blockage or irregularity in one or more of the cooling holes.

In the illustrated embodiment, the set-up of the imaging module 2 includes a fixture 7, including a table having suitable clamping means for securely holding the blade or vane 5 in position. For the purpose of imaging, the table preferably allows movement with all six degrees of freedom, including rotation along the direction 8 and swivel along the direction 9 as shown. A thermographic image of the blade or vane 5 is generated by passing a medium through the cooling holes 6 and capturing infra-red radiation emitted from the blade or vane 5 while the medium is flowing through the cooling holes 6. To that end, the set-up includes a first flow line 10 arranged for conducting a heated medium, such as hot air, into the hollow interior of the blade or vane 5. A suitable heating element 12 may be provided on the flow line 10. Furthermore, a second flow line 11 may be arranged for conducting a cooled medium into interior of the blade or vane 5. In this example, the cooled medium is cooled air provided by a chiller 15 provided on the flow line 11. Alternately, the cooled medium may comprise ambient air, which would not necessitate the chiller 15. The flow lines 10 and 11 are each connected to a flow control valve 13, such as a solenoid valve, which can be switched to alternately allow either the heated medium or the cooled medium to pass through the blade or vane 5. The heated or cooled medium would then traverse through the hollow interior of the blade or vane 5 and exit through the cooling holes 6 as shown in FIG. 1. The set-up further includes an infra-red imaging device 14 such as an infra-red radiometer, an infra-red camera, or the like, to capture infra-red radiation emitted from the blade or vane 5 while the heated or medium is flowing through the cooling holes 6.

In operation, the inspection of the cooling holes 6 of the blade or vane 5 begins with a heat-up cycle by switching solenoid valve 13 to a position to pass heated medium to the interior of blade or vane 5. In this case, air is heated by the heating element 12 to a temperature greater than ambient temperature to provide sufficient contrast in the infrared signature of the cooling holes 6 received by the infra-red imaging device 14 when the heated medium exits cooling holes 6. The heated medium is preferably forced into the hollow interior of blade or vane 5 for a predetermined time period to sufficiently heat the interior walls of blade or vane 5 and the walls surrounding cooling holes 6. This time period will vary depending upon the size of the blade or vane 5 but can be of a sufficient duration so that blade or vane 5 is heated to a steady state condition or so that the blade or vane material is heated to a sufficiently high temperature to cause a contrast in the infrared signature of the holes detected by the infra-red imaging device 14 when solenoid valve 13 is switched to provide the cooled medium to the interior of blade or vane 5 for the cool-down cycle.

A first infrared thermographic image (typically a first series of infra-red thermographic images) of the blade or vane 5 is generated by the infra-red imaging device 14 during the heat-up cycle.

After the heat-up cycle, solenoid valve 13 is switched to pass the cooled medium to the interior of blade or vane to start a cool-down cycle. The cooled medium used herein is cooled air preferably below ambient to improve the contrast or sensitivity of the infrared signature received by the infrared imaging device 14. A second infra-red thermographic image (typically a second series of infra-red thermographic images) of the blade or vane 5 is generated by infra-red imaging device 14 during the cool-down cycle.

The air streams 16 exiting cooling holes 6 during both the heat-up and cool-down cycles cause the cooling holes to act as black-body cavity radiators and as such, they approach behaving as idealized sources of radiation in accordance with Planck's well-known, empirically ascertained law.

Figure 4:
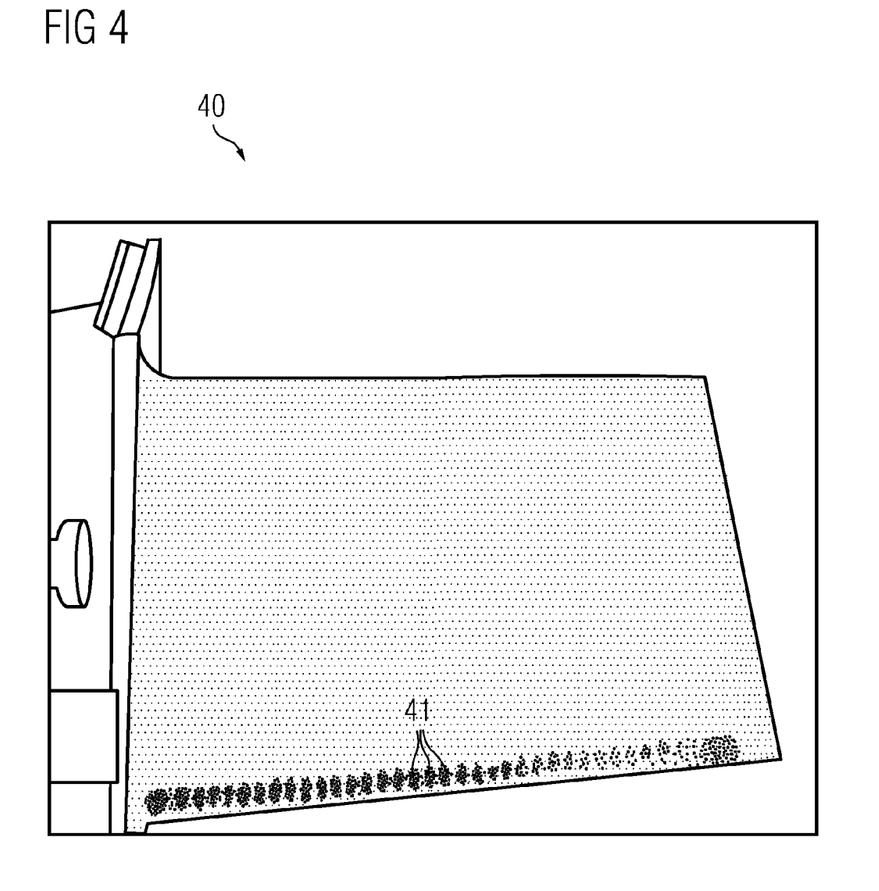
FIG. 4 illustrates a thermographic image of the component showing hot-spots that correspond to through-holes.

The thermographic images, thus obtained, are used for analyzing temperature distribution of the blade or vane 5, to inspect blockages or irregularities in the cooling holes 6. Each thermographic image is generated by assigning a different color to different temperatures of infra-red radiation captured by the imaging device 14. The temperature of a particular region in a thermographic image may thus be determined based on the color and/or the intensity (brightness) of that region. FIG. 4 shows an exemplary thermographic image 40 of a turbine blade. Herein, as shown, the regions 41 of maximum temperature (referred to as hot-spots) correspond in general to cooling holes. However, as can be seen, such a thermographic image has a high noise component, which, in combination with other reasons such as the small size and close spacing of the cooling holes, and inhomogeneous illumination in the thermographic images due to curvatures in the blade or vane 5, makes it difficult to isolate and analyze the temperatures of these hot spots 41 using standard image processing techniques.

The technique described below provides an automatic evaluation of a thermographic image to inspect blockages or irregularities in one or more of the cooling holes.

Referring back to FIG. 1, the first and second thermographic images (or first and second series of thermographic images) generated by the imaging module 2 are provided to the image processing module 3. Additionally, these images may be displayed on a display monitor 17. The image processing module 3 combines the first and second thermographic images (or first and second series of thermographic images) to generate a thermographic image of desired contrast. It should be noted herein that the purpose of thermographic imaging during a cool-down cycle following a heat-up cycle is to provide improved contrast or sensitivity of the infrared signature received by the infrared imaging device 14. However in an alternate embodiment, a thermographic image may be generated by passing a single medium, preferably a heated medium through the cooling holes, thus omitting the cool-down cycle completely.

Figure 2A:
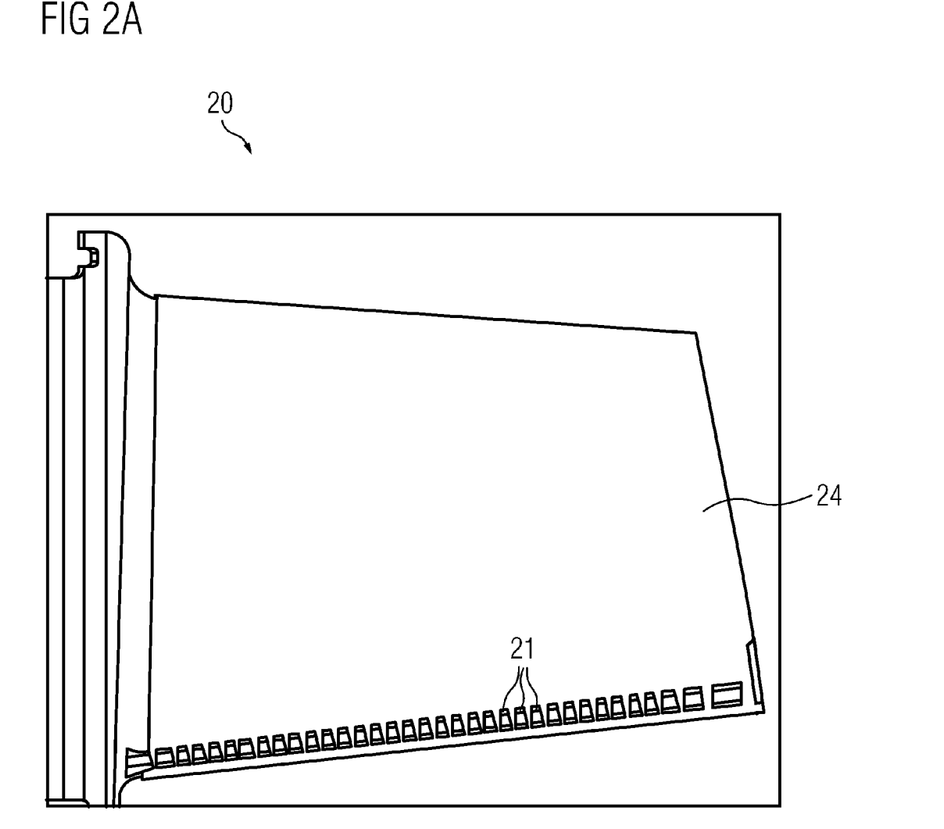
FIG. 2A illustrates a digital image of the component obtained from a 3D CAD model.

In accordance with the present invention, the thermographic image as obtained above is evaluated based on a correlation of the thermographic image to a digital image obtained from geometrical data of the blade or vane 5. Such a digital image may be obtained, as illustrated in this embodiment, from an already existing 3D CAD model of the blade or vane. FIG. 2A illustrates a three-dimensional (3D) digital image 20 obtained from a CAD model of the concerned turbine blade or vane. The image processing module correlates the thermographic image and the digital image from the CAD model to extract the regions corresponding to cooling holes from the thermographic image, as described below.

Figure 3:
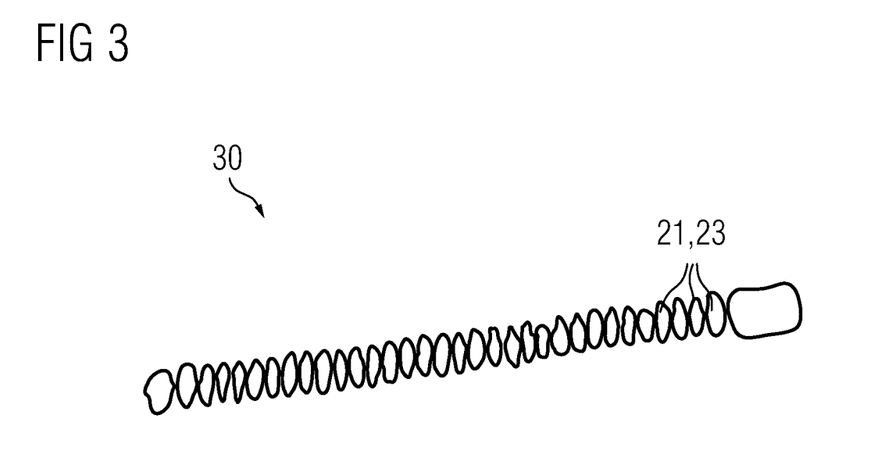
FIG. 3 illustrates a digital image mask for the regions corresponding to through-holes from CAD model or 3D measurement.

The first step involves the computation of a digital image mask for the positions 21 of the cooling holes on the digital image 20 (See FIG. 2A). The positions 21 of the cooling holes are determined from position data in the 3D CAD model. Furthermore, compensation of positional tolerances may be determined using best fit method. Using the position data of the cooling holes thus determined, a digital image mask is computed for the regions 21 corresponding to the positions of cooling holes in the digital image 20. Computation of the digital image mask involves setting the pixel values of all bits to '1' for the regions 21 in the digital image 20, and setting the pixel values of all bits to '0' in the surrounding background region 24, i.e., the remaining portion of the digital image 20. FIG. 3 shows a digital image mask 30 obtained as a result of the above operation.

The next step involves fitting the thermographic image on to the digital image. In the presently contemplated embodiment, the thermographic image 40 (see FIG. 4) is directly fitted on to the 3D image 20 (see FIG. 2A), which corresponds to the viewing position in the thermographic image. This embodiment is particularly advantageous if the clamping or positioning of the blade or vane 5 in the imaging module 2 (see FIG. 1) is reproducible, which allows the test set up to be calibrated or measured just once. In an alternate embodiment, to obviate difficulties in calibrating the test set up, the thermographic image may be fitted on to a two dimensional (2D) image calculated from the CAD model of the blade or vane that corresponds to the viewing position in the thermographic image.

Figure 5:
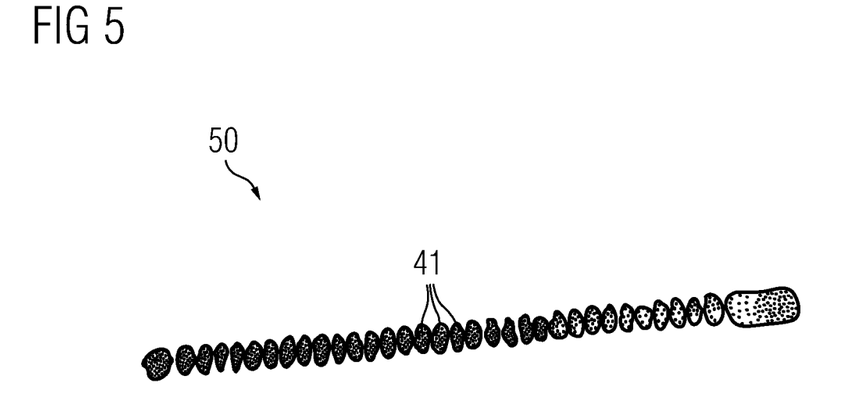
FIG. 5 illustrates a masked thermographic image wherein the regions corresponding to through-holes in the thermographic image of FIG. 4 are extracted.

From the fitted thermographic image, the hot spots or regions 41 corresponding to the cooling holes (see FIG. 4) are extracted by masking the fitted thermographic image using the computed digital image mask 30 (see FIG. 3). The process of masking the thermographic image involves a logical combination of the computed digital mask 30 (see FIG. 3) with the fitted thermographic image 40 (see FIG. 4) using a bitwise AND operation. The result, as shown in FIG. 5, is a masked thermographic image 50 isolating the regions 41 corresponding to cooling holes.

Referring back to FIG. 1, the masked thermographic image is provided to the analysis module 4 for inspection of blockages and irregularities in the cooling holes. Since the regions corresponding to the cooling holes (hot spots) are isolated and clearly distinguished from the background, it is possible to determine a blockage or irregularity, for example, by comparing the temperature values (determined based on color and/or brightness) for each of the isolated hot spots to a threshold or reference value.

The above technique is completely automatic and is considered to be advantageous over the subjective evaluation of thermographic images in the mentioned state of the art. The above-described embodiments of the present invention reduce the testing time and eliminate the need of trained staff for this purpose.

Figure 2B:
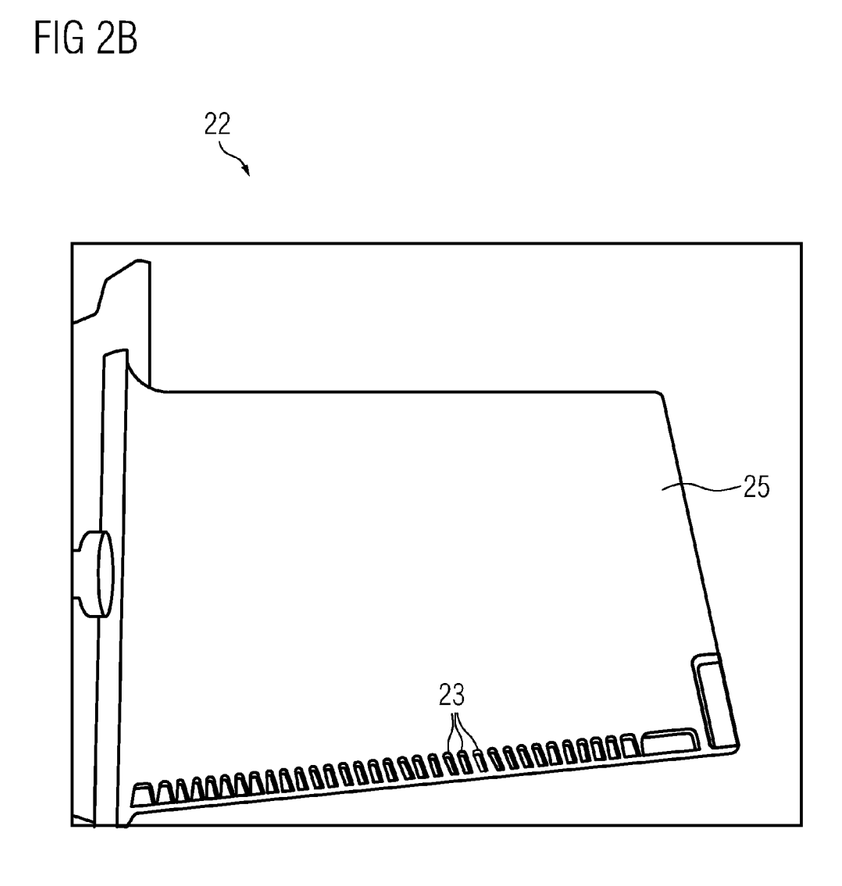
FIG. 2B illustrates a digital image of the component obtained from a 3D measurement of the component.
Figure 6:
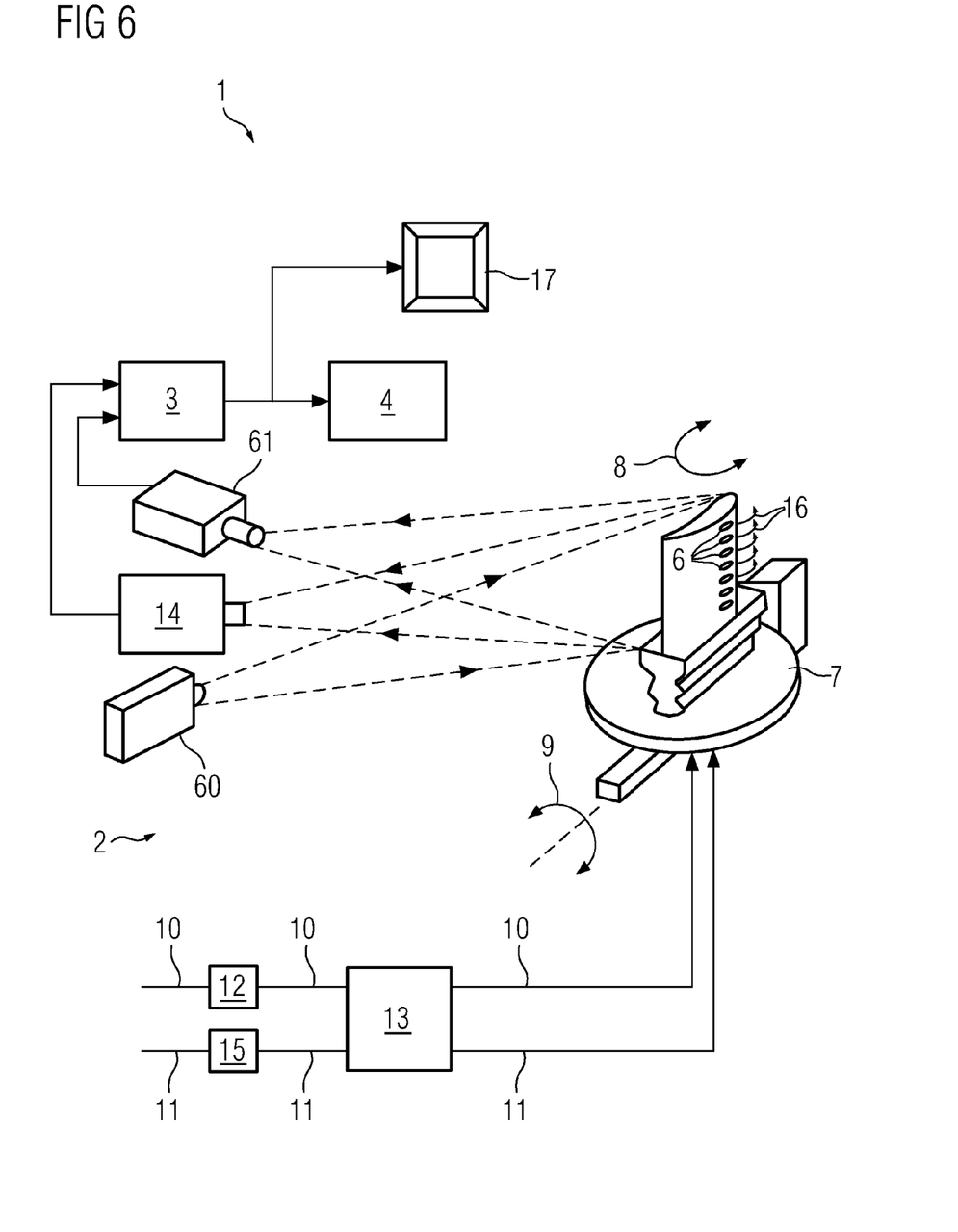
FIG. 6 is a schematic diagram of an apparatus for inspection of through-holes of a component, further including 3D imaging means in accordance with a further embodiment of the present invention.

In an alternate embodiment, instead of using a CAD model, the digital image is obtained from a 3D geometrical measurement of the blade or vane. Such a 3D image may be retrieved from an existing image database. However, in a preferred embodiment, the 3D image of the blade or vane is generated in-situ with the thermographic imaging set up. FIG. 6 illustrates an apparatus for achieving this. Herein, the imaging module 2 additionally includes 3D imaging means, comprising a light source, such as a structured light projector 60 and an image capturing device, such as a CCD (or CMOS) camera 61, arranged as proximate to the infra-red imaging device 14 shown. The shown arrangement advantageously allows the 3D measurement of the blade or vane to be carried out in the same viewing position as that of the thermographic image, for a given clamping position of the blade or vane 5. FIG. 2B shows an exemplary 3D digital image 22 of the turbine blade or vane 5 captured by the CCD (CMOS) camera 61, corresponding to the viewing position of the thermographic image 40 (see FIG. 4)

Referring back to FIG. 6, the 3D image captured by the CCD (or CMOS) camera 61 is provided to the image processing module 3, along with the thermographic image from the infra-red imaging device 14, for further processing.

The first step involves the computation of a digital image mask for the positions 23 of the cooling holes on the digital image 22 (see FIG. 2B). The positions 23 of the cooling holes are determined, for example by determining the positions depressions on the surface of the blade or vane in the 3D image 22 using standard image processing techniques. Using the position data of the cooling holes thus determined, a digital image mask is computed for the regions 23 corresponding to cooling holes in the digital image 22 as determined using said image processing techniques. Similar to the previously illustrated embodiment, the computation of a digital image mask herein involves setting the pixel values of all bits to '1' for the regions 23 in the digital image 22, and setting the pixel values of all bits to '0' in the surrounding background region 25, i.e., the remaining portion of the digital image 22. The resultant digital image mask is similar to that illustrated in FIG. 3.

The next step involves fitting the thermographic image on to the 3D digital image. In a preferred embodiment, the thermographic image 40 (see FIG. 4) is directly fitted on to the 3D image 22 (see FIG. 2B), which corresponds to the viewing position in the thermographic image. In an alternate embodiment, the thermographic image may be fitted on to a 2D image calculated from the 3D image of the blade or vane captured by the CCD (or CMOS) camera, that corresponds to the viewing position in the thermographic image.

From the fitted thermographic image, the hot spots or regions corresponding to the cooling holes are extracted by masking the fitted thermographic image using the computed digital image mask. Again, this step involves a logical combination of the computed digital mask with the fitted thermographic image using a bitwise AND operation. The result is a masked thermographic image isolating the regions corresponding to cooling holes similar to the one shown in FIG. 5.

Referring back to FIG. 6, the masked thermographic image is provided to the analysis module 4 for inspection of blockages and irregularities in the cooling holes, for example, by comparing the temperature values (determined based on color and/or brightness) for each of the isolated hot spots to a threshold or reference value, as mentioned above.

The inventive step involved in the above-described embodiment is to provide a method and apparatus for combining thermographic image data to 3D geometrical measurements. Advantageously, the above embodiment obviates the need for 3D models. Further, since the 3D geometric measurements are made in situ with thermal imaging, the above technique is not sensitive to deviations in the geometry of the component, i.e., the blade or vane. Furthermore, the above embodiment provides a universal test procedure with very little effort for setting up.

Referring to FIGS. 1 and 6, the image processing module 3 and the analysis module 4 may comprise one or more processors having hardware suitable for executing appropriate algorithms to implement the above-described methods. The functionalities of the image processing module 3 and the analysis module 4 are thus rendered by the algorithms executed by them. Thus, the present invention may also be embodied as a computer program product comprising computer readable media having computer readable program code stored therein, which, when executed on one or more processors, carries out the method according to any of the above-mentioned embodiments.

While this invention has been described in detail with reference to certain preferred embodiments, it should be appreciated that the present invention is not limited to those precise embodiments. Rather, in view of the present disclosure which describes the current best mode for practicing the invention, many modifications and variations would present themselves, to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

The invention claimed is:

1. A method for automatic inspection of a plurality of through-holes of a component, comprising:
    obtaining a thermographic image of the component generated by passing a medium through the plurality of through-holes and capturing infra-red radiation emitted from the component while the medium is flowing through the plurality of through-holes;
    generating a digital image from geometrical data of the component based on a viewing position of the thermographic image;
    determining positions of the plurality of through-holes by identifying depressions on a surface of the component in the digital image;
    computing a digital image mask for the determined positions of the plurality of through-holes on the digital image;
    fitting the thermographic image on the digital image obtained from geometrical data of the component;
    masking the fitted thermographic image using the digital image mask to extract regions corresponding to the plurality of through-holes in the thermographic image wherein the digital image mask is computed based on the determining of the positions of the plurality of through-holes on the digital image; and
    evaluating the masked thermographic image to determine an irregularity or blockage in one or more of the plurality of through-holes, wherein computing the digital image mask involves setting pixel values of all bits to '1' for a region corresponding to the positions of the through-holes on the digital image and setting pixel values of all bits to '0' in the remaining portion of the digital image and the masking the fitted thermographic image involves a logical combination of the digital image mask with the fitted thermographic image using a bitwise AND operation.

2. The method according to claim 1, wherein the digital image is obtained from a Computer-Aided Design model of the component.

3. The method according to claim 1, wherein the digital image is obtained from a three-dimensional geometrical measurement of the component.

4. The method according to claim 3, wherein the three-dimensional geometrical measurement of the component is made in-situ with the capturing of the thermographic image and at a viewing position that corresponds to the viewing position of the thermographic image.

5. The method according to claim 1, wherein the step of fitting comprises fitting the thermographic image directly on a three-dimensional digital image of the component.

6. The method according to claim 1, wherein the step of fitting comprises fitting the thermographic image on a two-dimensional digital image of the component corresponding to the viewing position of the thermographic image.

7. The method according to claim 1, wherein a blockage or irregularity in a through-hole is determined by comparing a temperature of the region corresponding to the through-hole determined from the masked thermographic image to a reference temperature value.

8. The method according to claim 1, wherein the masked thermographic image is obtained by combining multiple thermographic images including at least a first and a second thermographic image, wherein the first thermographic image is generated by passing a heated medium through the plurality of through-holes during a heat-up cycle and capturing infra-red radiation emitted from the component during the heat-up cycle, and the second thermographic image is generated by passing a cooled medium through the plurality of through-holes during a cool-down cycle and capturing infra-red radiation emitted from the component during the cool-down cycle.

9. The method according to claim 1, wherein the component is a turbomachine blade or vane, and wherein the plurality of through-holes are cooling holes.

10. A non-transitory computer readable media, comprising:
a non-transitory computer readable media having computer readable program code embodied therein, which, when executed on a processor, carries out the method according to claim 1.

11. An apparatus for automatic inspection of a plurality of through-holes of a component, comprising:
an imaging module adapted for generating a thermographic image of the component by passing a medium through the plurality of through-holes and capturing infra-red radiation emitted from the component while the medium is flowing through the plurality of through-holes;
an image processing module, comprising a processor, adapted for generating a digital image from geometrical data of the component based on a viewing position of the thermographic image, determining positions of the plurality of through-holes by identifying depressions on a surface of the component in the digital image, computing a digital image mask for the determined positions of the plurality of through-holes on the digital image, fitting the thermographic image on the digital image previously obtained from geometrical data of the component, and for masking the fitted thermographic image using the digital image mask to extract regions corresponding to the plurality of through-holes in the thermographic image, the digital image mask being computed based on the determined positions of the plurality of through-holes on the digital image; and
an analysis module, comprising a processor, adapted for evaluating the masked thermographic image to determine an irregularity or blockage in one or more of the plurality of through-holes,
wherein computing the digital image mask involves setting pixel values of all bits to '1' for a region corresponding to the positions of the through-holes on the digital image and setting pixel values of all bits to '0' in the remaining portion of the digital image and the masking the fitted thermographic image involves a logical combination of the digital image mask with the fitted thermographic image using a bitwise AND operation.

12. The apparatus according to claim 11, wherein the digital image is obtained from a Computer-Assisted Design model of the component.

13. The apparatus according to claim 11, wherein the imaging module further comprises a three-dimensional imaging means for generating the digital image, based on a three-dimensional geometrical measurement of the component from a viewing position that corresponds to the viewing position of the thermographic image.

14. The apparatus according to claim 11,
wherein the masked thermographic image is obtained by combining multiple thermographic images including at least a first and a second thermographic image, and
wherein the imaging unit further comprises:
a first arrangement for passing a heated medium through the plurality of through-holes during a heat-up cycle,
a second arrangement for passing a cooled medium through the plurality of through-holes during a cool-down cycle, and
an infrared imaging device for capturing infra-red radiation emitted from the component during the heat-up and cool-down cycles, to respectively generate the first and the second thermographic image.

15. The apparatus according to claim 11, wherein the analysis module is adapted to determine a blockage or irregularity in a through-hole by comparing a temperature of the region corresponding to the through-hole, as determined from the masked thermographic image, to a reference temperature value.

* * * * *